United States Patent [19]

Rinehart et al.

[11] Patent Number: 4,908,445

[45] Date of Patent: Mar. 13, 1990

[54] SESQUITERPENE COMPOUNDS AND PHARMACEUTICAL COMPOSITIONS CONTAINING SAME, FROM PACHASTRELLA SPONGES

[75] Inventors: Kenneth L. Rinehart, Urbana, Ill.; Ashok D. Patil, King of Prussia, Pa.

[73] Assignee: Harbor Branch Oceanographic Institution, Inc., Ft. Pierce, Fla.

[21] Appl. No.: 295,145

[22] Filed: Jan. 9, 1989

[51] Int. Cl.⁴ .................. C07D 211/54; C07D 309/38; C07D 315/00
[52] U.S. Cl. .................. 540/527; 546/243; 549/294; 549/425
[58] Field of Search .................. 514/213, 349, 460; 546/243; 549/425, 294; 540/527

[56] References Cited

PUBLICATIONS

De Moraes et al., Bol. Inst. Oceanogr. 27(2), 57–78
Biological Abstract, vol. 69, No. 3655.

Primary Examiner—Mukund J. Shah
Assistant Examiner—E. C. Ward
Attorney, Agent, or Firm—Carroll F. Palmer

[57] ABSTRACT

A new class of novel, biologically active sesquiterpene compounds, pharmaceutical compositions containing them, methods of producing the compounds and compositions and methods of using them are disclosed. This new class of compounds have the generic formulae:

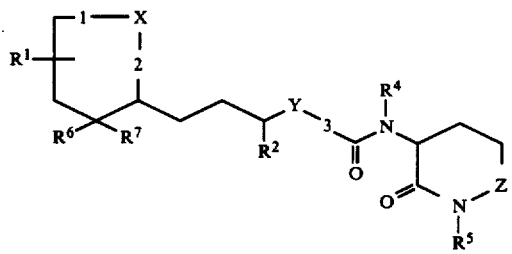

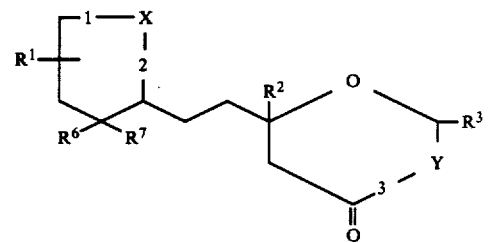

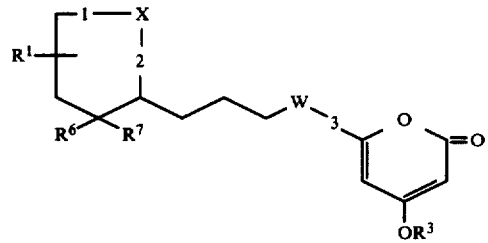

wherein $X = -1-CH_2-\underset{\underset{CH_2}{\|}}{C}-2- \text{ or } -1-CH=\underset{\underset{CH_3}{|}}{C}-2-$ $Y = -CH_2-3- \text{ or } =CH-3-$ $Z = -CH_2- \text{ or } -CH_2-CH_2-$ $W = -\underset{\underset{R^1}{|}}{CH}-3- \text{ or } =\underset{\underset{R^1}{|}}{C}-3-$ and
$R^1, R^2, R^3, R^4, R^5, R^6, R^7 = H$ or lower alkyl.

26 Claims, No Drawings

SESQUITERPENE COMPOUNDS AND PHARMACEUTICAL COMPOSITIONS CONTAINING SAME, FROM PACHASTRELLA SPONGES

FIELD OF THE INVENTION

This application relates to novel sesquiterpene compounds and compositions containing such compounds as active ingredients. More particularly, the invention concerns a new class of biologically active sesqui terpene compounds, pharmaceutical compositions containing them, methods of producing the compounds and compositions and methods of using them.

BACKGROUND OF THE INVENTION

The prevention and control of viral diseases are of prime importance to man and much research has been devoted to development of antiviral measures. Certain methods and chemical compositions have been developed which aid in inhibiting, controlling or destroying viruses, but additional methods plus antiviral compositions are needed.

It has been found that some natural products and organisms are potential sources for chemical molecules having useful biological activity of great diversity. Marine have proved to be such a source and a number of pubications have issued disclosing organic compounds derived from marine sponges including Scheuer, P. J. Ed., Marine Natural Products, Chemical and Biological Perspectives; Academic Press, New York, 1978, Vol. I, pp 175–240; Faulkner, D. J., Nat. Prod. Rep. 1987, 4, 539–576 and references cited therein; Uemura, D. et al., J. Am. Chem. Soc., 1985, 107, 4796–4798; Minale, L. et al., Fortschr. Chem. org. Naturst. 1976, 33, 1–72.

This present invention, utilizing sponges as a source material and supplemented by novel synthetic production methods, has provided the art with a new class of biologically active compounds and new pharmaceutical compositions useful as antiviral agents.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects of the invention are accomplished by the provision of a novel class of biologically active compounds that have a structure according to the formulae:

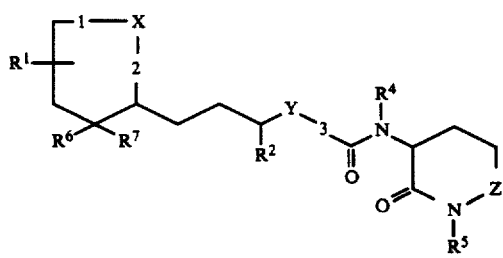

I

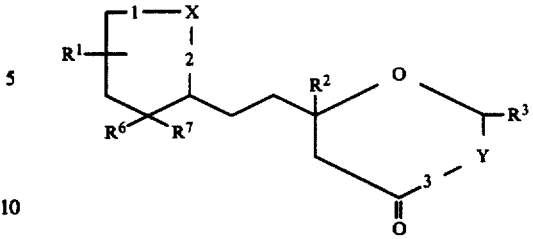

II

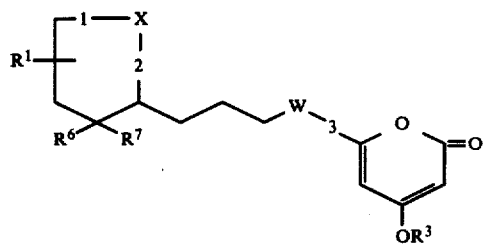

III wherein

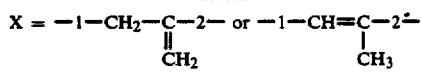

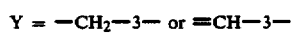

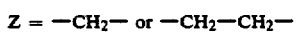

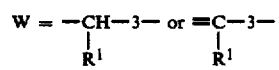

$R^1, R^2, R^3, R^4, R^5, R^6, R^7 = H$ or lower alkyl.

As a result of the discoveries by the invention of the new compounds as delineated above, skilled chemists will be able to use procedures as disclosed herein and others to synthesize these compounds from available stock substances. In preferred embodiments, the compounds are in substantially pure form, i.e., contain at least 95% thereof.

As embodied and fully described herein, the invention also comprises pharmaceutical compositions, e.g., antiviral compositions, containing as active ingredient, an effective amount, preferably between about 0.1 and 45% by weight based on the total weight of the composition, especially between about 1 and 25% b/w, of one or more compounds according to the formulae expressed above and a non-toxic pharmaceutically acceptable carrier or diluent.

As embodied and fully described herein, the invention also comprises processes for the production of the new compounds and compositions of the invention and methods of use thereof, e.g., methods of inhibiting or destroying viruses.

In accordance with the invention, methods for inhibiting and destroying viruses comprise administering to the host an effective amount of new pharmaceutical compositions of the invention.

DESCRIPTION OF THE PREFERRED EMBODIMENTS

A more complete understanding of the invention can be obtained by reference to preferred embodiments of the specific examples of compounds, compositions and methods of the invention. It will be apparent to those skilled in the art that the examples involve use of materials and reagents that are commercially available from known sources, e.g., chemical supply houses, so no details are given respecting them.

One method of preparation of the new compounds of the invention involves extraction from marine sponges of the genus Pachastrella (order Choristida), voucher samples of which have been deposited under the identification numbers SPBE 10-XII-84-3-30 and SPBE 10-XII-84-3-32 in the Indian River Coastal Zone Museum of Harbor Branch Oceanographic Institution at Ft. Pierce, Fla.

EXAMPLE 1

This example concerns the preparation of compounds 1 and 2 of the invention having the following formulae:

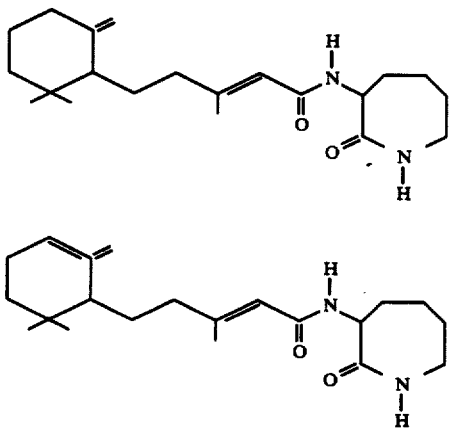

A quantity of small, amorphous sponge Pachastrella sp. with purple ectosome and gray endosome was collected by a submersible at Club Cay, Bahamas at a depth of 2500 feet. The sponge (10-XII-84-3-30) was bioassayed, then immediately frozen. Later, the frozen sample was chopped, homogenized in a blendor with methanol, filtered, steeped in fresh methanol and filtered. The combined extracts were evaporated under vacuum to 30° C. to give a pale-brown residue that was successively triturated with hexane and methylene chloride to yield two extracts both of which showed antiviral activity vs. *Herpes simplex* virus type 1 (HSV-1) and *Vesicular stomatitis* virus (VSV). TLC examination of both extracts revealed essentially identical compositions, and both had the same foul smell; hence, they were combined to give extract I.

Similar treatment of another sponge sample (10-XII-84-3-32) collected in similar manner at the same site gave a pale-brown residue. Further extraction yielded a hexane extract and a methylene chloride extract, both bioactive, which were combined as extract II.

The residue from extract I was chromatographed over a column of silica gel, eluting with methylene chloride, then with increasing precentages of methanol in methylene chloride. Fractions (61 from extract I and 140 from extract I) were collected and pooled according to their TLC behavior. Fractions 12–24 eluted with MeOH:CH$_2$Cl$_2$ (2:98) were subjected to PTLC (Me$_2$CO:C$_6$H$_6$:1:3) to give 1 and 2.

Compound 1 exists as shiny needles, mp 129° C.; [α]$^{20}$D+46.8° (c 1.7, CHCl$_3$); UV λmax (Et$_2$O) 204, 217 nm; IR (CHCl$_3$) 3414, 1657, 1477, 1333, 1228 cm$^{-1}$; $^1$H NMR (200 MHz, CDCl$_3$) δ6.80 (br d, J=4 Hz, D$_2$O exch), 6.11 (br t, D$_2$O exch), 5.63 (d, J=<1 Hz), 4.78 (s), 4.54 (m), 4.54 (s), 3.28 (m), 2.15 (d, J=<1 Hz), 2.15–1.11 (m), 2.15, 1.50, 0.92 (s), 0.84 (s); $^{13}$C NMR (200 MHz, CDCl$_3$) 175.7 (s), 165.6 (s), 154.8 (s), 148.2 (s), 117.0 (d), 108.7 (t), 53.0 (d), 51.2 (d), 41.4 (t), 38.6 (t), 35.5 (s), 34.3 (t), 31.7 (t), 31.2 (t), 28.2 (t), 27.7 (q), 27.4 (t), 25.7 (q), 23.7 (t), 23.0 (t), 17.8 (q). EIMS m/z 346 (M, 10, also by FDMS), 313 (5), 223 (13), 218 (9), 176 (26), 129 (100), 95 (60); HREIMS m/z 129.1029 (C$_6$H$_{13}$N$_2$O requires 129.1027).

Anal. Calcd for C$_{21}$H$_{34}$N$_2$O$_2$ (M): 346.2620. Found 346.2616 (HREIMS).

Compound 2 is a colorless granular solid, containing ca. 10% of 1, mp 121°–123° C.; [α]$^{25}$D+75.4° (c 1.1, CHCl$_3$); UV λmax (Et$_2$O) 205, 217 nm; IR (CHCl$_3$) 3414, 1657, 1477, 1330, 1230 cm$^{-1}$; $^1$H NMR (200 MHz, CDCl$_3$) δ7.27 (t, D$_2$O exch), 6.89 (br d, J=5 Hz, D$_2$O exch), 5.54 (br s), 5.21 (t), 4.45 (m), 3.17 (m), 2.06 (s), 1.57 (d, J=1.9 Hz), 0.83 (s), 0.77 (s); $^{13}$C NMR (200 MHz, CDCl$_3$) 176.0 (s), 165.9 (s), 155.1 (s), 1.35.7 (s), 120.2 (d), 117.4 (d), 51.5 (d), 48.6 (d), 41.8 (t), 41.2 (t), 32.3 (t), 31.6 (t), 31.3 (t), 28.9 (t), 28.6 (t), 27.8 (t), 27.3 (q), 27.2 (t), 23.2 (q), 22.7 (t), 18.2 (q). EIMS m/z 346 (M, 3, also by FMDS), 223 (17), 218 (4), 217 (10), 171 (14), 170 (24), 129 (75), 95 (100); HREIMS m/z 129.1030 (C$_6$H$_{13}$N$_2$O requires 129.1027), 95.0497 (C$_6$H$_7$O requires 95.0496).

Anal. Found for C$_{21}$H$_{34}$N$_2$O$_2$ (M): 346.2619 (HREIMS)

EXAMPLE 2

This example concerns the preparation of compound 3 of the invention having the following formula:

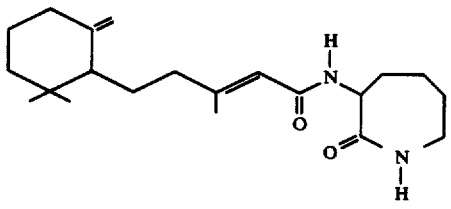

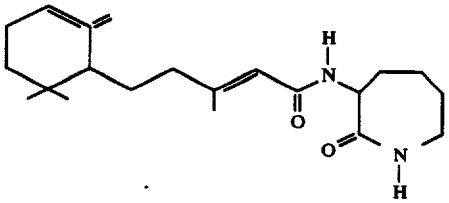

Fractions 25–42 derived as stated in Example 1 from extract I eluted with MeOH:CH$_2$Cl$_2$ (3:97) after chromatography over a column of silica gel (Me$_2$CO:C$_6$H$_6$:3:7) yielded a mixture of isomers 1 and 2 and 3.

Compound 3 is a colorless gum; IR (CHCl$_3$) 3414, 2950, 1651, 1540, 1500, 1470 cm$-$1, $^1$H NMR (200 MHz, CDCl$_3$) δ6.85 (d, J=4 Hz, D$_2$O exch), 6.23 (br t, D$_2$O exch), 4.72 (br s), 4.53 (m), 4.51 (br s), 3.25 (m), 2.25–0.90 (m), 0.91 (d, J=6 Hz), 0.90 (s), 0.83 (s); $^{13}$C NMR (200 MHz, CDCl$_3$) 175.6 (s), 171.8 (s), 149.4 (s), 108.8 (t), 54.0 (d), 52.0 (d), 44.7 (t), 42.2 (t), 36.1 (t), 35.2 (s), 34.9 (t), 32.3 (t), 31.7 (t), 30.9 (d), 28.9 (t), 27.9 (q), 27.9 (t), 26.3 (q), 23.7 (t), 23.5 (t), 19.5 (q).; FDMS m/z 348 (M); FABMS m/z 349 (M+H).

Anal. Calcd for $C_{21}H_{37}N_2O_2$: 349.2854 (M+H). Found 349.2943 (HRFABMS)

EXAMPLE 3

This example concerns the preparation of compounds 4 and 5 of the invention having the following formulae:

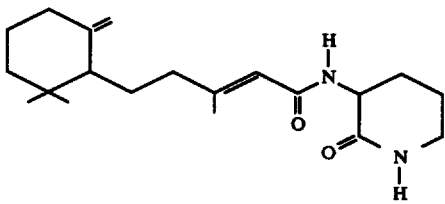

4

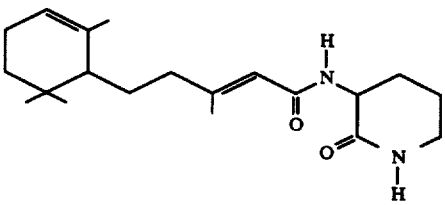

5

Fractions 43-61 derived as stated in Example 1 from extract I eluted with MeOH:CH$_2$Cl$_2$ (1:24) contained a mixture of isomers 4&5. These were purified by PTLC (SiO$_2$, Me$_2$CO:C$_6$H$_6$: 3:7) and RP-HPLC (H$_2$O:MeOH: 1:9) and separated by silver nitrate-impregnated silica gel chromatography (Me$_2$CO:C$_6$H$_6$: 3:17) giving 4 and 5.

Compound 4 exists as shiny needles from C$_6$H$_{14}$-EtOAc, mp 92°-93° C.; $[\alpha]^{20}D$ -39.1° (c 3.8, CHCl$_3$); UV λmax (Et$_2$O) 205, 217 nm; IR (CHCl$_3$) 3404, 3022, 1662, 1491, 1203 cm$^{-1}$; $^1$H NMR (200 MHz, CDCl$_3$) δ6.45 (d, J=5 Hz, D$_2$O exch), 6.35 (br t, D$_2$O exch), 5.61 (d, J=<1 Hz), 4.78 (br s), 4.52 (br s), 4.32 (p), 3.36 (m, D$_2$O exch), 2.60 (m), 2.16 (m), 2.15 (d, J=<1 Hz), 2.15, 2.10-0.90 (m), 1.60, 0.91 (s), 0.87 (s); $^{13}$C NMR (200 MHz, CDCl$_3$) 172.2 (s), 166.9 (s), 155.0 (s), 148.5 (s), 117.1 (d), 108.9 (t), 54.1 (d), 49.8 (d), 41.2 (t), 34.6 (t), 34.5 (s), 28.4 (t), 28.0 (t), 27.3 (q), 24.2 (t), 24.0 (q), 23.3 (t), 23.2 (t), 18.2 (q). EIMS m/z 332 (M, 2, also by FDMS), 317 (3), 218 (5), 209 (22), 156 (39), 115 (67) 95 (100); HREIMS m/z 115.0872 (C$_5$H$_{11}$N$_2$O requires 115.0871), 95.0498 for C$_6$H$_7$O.

Anal. Calcd for $C_{20}H_{32}N_2O_2$ (M): 332.2463. Found 332.2462 (HREIMS)

Compound 5 exists as colorless crystals, mp 67°-70° C.; $[\alpha]^{20}D$ -57.60° (c 1.7, CHCl$_3$); UV λmax (Et$_2$O) 205, 217 nm; IR (CHCl$_3$) 3404, 3022, 1662, 1491, 1203 cm$^{-1}$; $^1$H NMR (200 MHz, CDCl$_3$) δ6.33 (d, J=5 Hz, D$_2$O exch), 5.93 (br t, D$_2$O exch), 5.61 (d, J=<1 Hz), 5.32 (br t), 4.32 (m), 3.36 (m), 2.61 (m), 2.15 (d, J=<1 Hz), 2.10-0.90 (m), 1.68 (d, J=<1 Hz), 0.94 (s), 0.89 (s); $^{13}$C NMR (200 MHz, CDCl$_3$) 172.9 (s), 167.7 (s), 156.0 (s), 136.5 (s), 120.9 (d), 118.0 (d), 50.7 (d), 49.4 (d), 41.9 (t), 41.6 (t), 33.0 (t), 32.0 (s), 29.6 (t), 28.0 (q), 27.9, 23.9 (q), 23.4 (t), 21.5 (t), 19.0 (q). EIMS m/z 332 (M, 2, also by FDMS), 209 (20), 196 (13), 156 (30), 115 (52), 95 (100); HREIMS m/z 115.0872 for C$_5$H$_{11}$N$_2$O, 95.0498 for C$_6$H$_7$O.

Anal. Found for $C_{20}H_{32}N_2O_2$ (M): 332.2465 (HREIMS).

EXAMPLE 4

This example concerns the preparation of compounds 6, 7&8 of the invention having the following formulae:

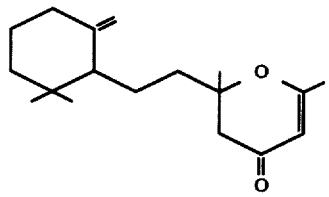

6

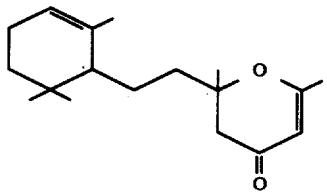

7

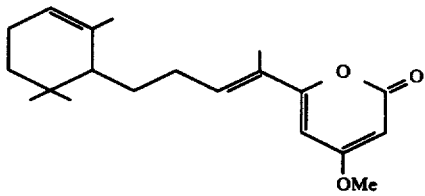

8

Fractions 1-11 derived as stated in Example 1 from extract I (eluted with methylene chloride) yielded an oil which was further purified by silica gel column chromatography followed by HPLC (SiO$_2$, EtOAc:hexane: 1:4) to provide a mixture of isomers 6 and 7 as an oil and 8 as a low-melting solid.

The mixture of isomers 6 and 7 was chromatographed over a column of silver nitrate-impregnated silica gel using EtOAc-hexane (7:93). About 50 fractions were collected and alternate fractions were monitored by their $^1$H NMR spectra. In this manner, pure samples of 6 and 7 were obtained, with 7 eluted first.

Compound 6 is an oil; $[\alpha]^{20}D$ -9.6° (c 1.5, CHCl$_3$); UV λmax (Et$_2$O) 255, 203 nm; IR (CHCl$_3$) 2959, 1653, 1606, 1396 cm$^{-1}$; $^1$H NMR (200 MHz, CDCl$_3$) δ5.29 (d, J=<1 Hz), 4.78 (s), 4.54 (s), 2.52 (d, J=17 Hz), 2.32 (d, J=17 Hz), 1.96 (s), 1.36 (s), 0.87 (s), 0.85 (s); $^{13}$C NMR (200 MHz, CDCl$_3$) 192.9 (s), 172.5 (s), 148.4 (s), 109.1 (t), 102.9 (d), 82.8 (s), 53.7 (d), 46.0 (t), 38.4 (t), 34.3 (t), 33.0 (s), 28.1 (q), 25.8 (q), 24.1 (t), 23.3 (q), 23.3 (t), 21.3 (q). EIMS m/z 276 (M, 5, also by FDMS), 125 (100), 95 (14), 85 (40), 81 (28); HREIMS m/z 125.0601 (C$_7$H$_9$O$_2$ requires 125.0602).

Anal. Calcd for $C_{18}H_{28}O_2$ (M): 276.2089. Found: 276.2091 (HREIMS).

Compound 7 is an oil; $[\alpha]^{25}D$ -100.8° (c 5.6, CHCl$_3$); UV λmax (Et$_2$O) 255, 202 nm; IR (CHCl$_3$) 2559, 1653, 1606, 1396 cm$^{-1}$; $^1$H NMR (200 MHz, CDCl$_3$) δ5.30 (t), 5.29 (d, J=<1 Hz), 2.52 (d, J=17 Hz), 2.32 (d, J=17 Hz), 2.00-0.90 (m), 1.96 (s), 1.66 (d, J=1.6 Hz), 1.36 (s), 0.91 (s), 0.87 (s); $^{13}$C NMR (200 MHz, CDCl$_3$) 193.1 (s), 172.6 (s), 136.3 (s), 121.1 (d), 103.8 (d), 83.7 (s), 49.5 (d), 45.9 (t), 39.7 (t), 32.3 (s), 32.2 (t), 28.1 (q), 28.0 (q), 24.9 (t), 23.8 (q), 23.8 (t), 22.0 (q). EIMS m/z (rel intensity) 276 (M, 6, also by FDMS), 261 (3), 161 (4), 153 (9), 136 (13), 125 (100); HREIMS m/z 151.1486 ($C_{11}H_{19}$ requires 151.1482), 125.0601 for $C_7H_9O_2$.

Anal. Found for $C_{18}H_{28}O_2$ (M): 276.2089 (HREIMS).

Compound 8 is a crystalline solid, mp 44° C.; $[\alpha]^{20}D$ −121.6° (c 3.7, $CHCl_3$); UV λmax ($Et_2O$) 317, 223 nm; IR ($CHCl_3$) 3024, 1701, 1645, 1554, 1454 cm$^{-1}$; $^1$NMR (200 MHz, $CDCl_3$) δ5.79 (t), 5.76 (d, J=1.6 Hz), 5.43 (d, J=1.6 Hz), 5.32 (m), 3.80 (s), 2.25–1.11 (m), 2.21 (m), 2.12 (d, J=<1 Hz), 0.94 (s), 0.88 (s); $^{13}$C NMR (200 MHz, $CDCl_3$) 171.0 (s), 164.0 (s), 160.0 (s), 150.5 (s), 135.7 (s), 120.3 (d), 116.4 (d), 100.5 (d), 87.1 (d), 55.5 (q), 48.6 (d), 42.0 (t), 32.3 (t), 32.3 (s), 29.1 (t), 27.3 (q), 23.7 (t), 23.2 (q), 19.2 (q). EIMS m/z (rel intensity) 316 (M, 2, also FDMS), 301 (1), 180 (20), 153 (10), 109 (27), 81 (83), 41 (100).

Anal. Calcd for $C_{20}H_{28}O_3$ (M): 316.2038. Found: 316.2040 (HREIMS).

EXAMPLE 5

This example concerns the work-up of extract II. A portion of the residue from sponge sample 10-XII-84-3-32 was chromatographed over a silica gel column (Kieselgel-60, 230–400 mesh, 80 g; $MeOH:CH_2Cl_2$: 1:39) with monitoring by TLC. Fractions 11–22 were combined and repurified by HPLC ($SiO_2$, EtOAc:hexane: 1:4) to provide 6 and 7 as a mixture and 8. Column chromatography over silver nitrate-impregnated silica (EtOAc:hexane: 7:93) provided pure 6 and 7.

Fractions 23–47, after PTLC ($Me_2CO:C_6H_6$: 1:4) followed by silver nitrate-impregnated silica column chromatography ($Me_2CO:C_6H_6$: 1:4) gave 1 and 2.

Fractions 48–80, after crystallization from EtOAhexane, provided shining needles containing 4+5, which were subjected to silver nitrate-impregnated silica chromatography ($Me_2CO:C_6H_6$: 15:85) to yield 4 and 5.

The mother liquor from the needles, after evaporation of solvent, gave a residue which was combined with fractions 81–140. The gum after silica gel chromatography ($Me_2CO:C_6H_6$: 3:7) yielded pure 7 and a mixture of isomers 4 and 5.

EXAMPLE 6

This example concerns the hydrolysis of compounds of the invention.

Hydrolysis of a portion of 1 with distilled 6N HCl was carried out in a sealed thick-walled glass tube at 110° C. for 24 hrs. The solvent was removed under reduced pressure at 55° C. and the colorless residue containing several compounds (TLC, $SiO_2$, $MeOH:CH_2Cl_2$: 7:93) was dissolved in water and extracted with methylene chloride. Removal of solvent from the organic layer followed by treatment with excess ethereal diazomethane provided a methyl ester: FDMS, EIMS m/z 250 (M). The dried aqueous layer gave L-lysine hydrochloride: white powder; $[\alpha]^{25}D$ +18.7° (c 7.1, 6N HCl); $R_f$=0.15 ($SiO_2$, n-BuOH:AcOH:$H_2O$: 6:4:1), identical with that of an authentic sample; FDMS m/z 147 (M+H); EIMS m/z 146.

L-lysine hydrochloride obtained by hydrolysis of 1 dissolved in 3N HCl in 1-butanol and heated at 100° C. for 30 min in a vial. The resulting solution was evaporated on a water bath under vacuum at 50° C. and residual solvent was removed by azeotroping with methylene chloride to give a gum which was dissolved in trifluoroacetic anhydride. The vial was capped and heated on an oil bath at 130° C. for 10 min, then allowed to cool (r.t.). Solvent was removed and purification by preparative TLC ($SiO_2$, $MeOH:CH_2Cl_2$: 1:99) gave the N-TFA n-butyl ester derivative.

Hydrolysis of 2 with distilled 6N HCl was carried out as for 1, and the organic layer was treated in the same way to provide the same methyl ester (EIMS). The dried aqueous layer yielded L-lysine hydrochloride.

Hydrolysis of 3 with distilled 6N HCl was carried out as for 1, and the organic layer was treated in the same way to provide a methyl ester: EIMS m/z 252. The dried aqueous layer yielded L-lysine hydrochloride.

Hydrolysis of 4 with distilled 6N HCl was carried out as for 1, and the organic layer was treated in the same way to provide the same methyl ester as from 1 and 2 (FD and EIMS). The dried aqueous layer furnished L-ornithine hydrochloride which was converted as for lysine from 1 above to its N-TFA n-butyl ester derivative.

The following assay methods were utilized to illustrate the biological activities of the compounds of the invention. Antiviral Disc Assay for HSV-1 and VSV

A. Maintenance of Cell Cultures

1. Virus a. *Herpes simplex*, type 1 (HSV-1) and *Vesicular stomatitis* viruses replicate in the CV-1 cell line. CV-1 is a fibroblast-like cell culture derived from primary African green monkey cells.

2. Growth of CV-1 Cells a. Seed 150-cm$^2$ tissue culture flasks each with $10 \times 10^6$ CV-1 cells in 40 ml of Eagles minimum essential medium (EMEM) with 10% fetal bovine serum (FBS, growth medium).

b. Seven days after seeding the flasks, cell numbers should be approximately $40-50 \times 10^6$. CV-1 cells have a doubling time of 72 hours based on these numbers.

3. Trypsinization a. Aseptically remove the medium b. Rinse cell sheet two time with 10 ml of Ca++− and Mg++− free Dulbecco's phosphate buffered saline.

c. Add 1.5 to 2.0 ml of trypsin—EDTA mixture.

d. Incubate flask at room temperature for 10 minutes.

e. Shake flask.

f. Add 10 EMEM growth medium and break up cell clumps with pipetting.

g. Count cells.

B. Preparation of plates for viral assays.

Cell Concentration a. Dilute the cells with EMEM to $4 \times 10^5$ cells/ml.

b. Seed 24-well trays with 0.5 ml per well. Cell concentration is $2 \times 10$ cells.

c. Incubate at 37° C. for 1.5 hrs.

d. The wells can be used over the next several days beginning the day after seeding (preferably 2, 3, or 4).

C. Assay of HSV-1 & VSV in CV-1 cells.

Infection of CV-1 cells in plates with virus a. Remove medium from wells.

b. Infect well with at least 25 and no more than 80 plaque-forming units (PFU) of virus.

c. Incubate infected cells at 37° C. for 1.5 hrs.

d. Pour off supernatant at end of incubation period.

e. Add 0.5 ml of methylcellulose overlay medium (MCO). MCO is a maintenance medium without phenol red made with 1% 4000 centipose methylcelluose. FBS is used at 5% level.

Drug Evaluation a. For drug evaluation wet filter paper discs (6 mm dia.) with approx. 0.02 ml of test compound. Allow solvent to evaporate for 20–30 mins. at ambient temperature, then place discs in the well containing CV-1 cells, virus and MCO.

b. Incubate tissue culture plates for 48 hrs. at 37° C.

c. After 48 hrs. place 0.5 ml NRMCO on each well. (NRMCO is maintenance overlay medium without phenol red containing 0.1 mg neutral red dye/ml and 2% Cps. methylcellulose).

d. Incubate plates at 37° C. and read the following day. Antiviral activity should be observed from two parameters. One is actual reduction in the number of plaques and two is the diminution in plaque diameter.

Scoring Drug Activity

Antiviral activity (AVA) is scored from 0 to +++.
+++ = 50–75% inhibition of plaque formation
++ = 25–50% inhibition
+ = <25% inhibition
0 = no protection Antiviral Assay for Mouse Coronavirus Strain A59

When NCTC 1469 cells (a clone of mouse liver cells) are infected with mouse coronavirus A59, the cytopathic effects (CPE) which regulate are characterized by giant cell formation, cell fusion, and cell destruction. Cell fushion observed in NCTC 1469 cell cultures infected can be observed microscopically in 12 hours and when stained with methylene blue dye the syncytia are visible to the eye as dark blue foci on the fixed cell sheet. Twenty-four hours after infection, cell fushion and cytopathic effects are extensive and the assays can be read both macroscopically and microscopically. Compounds with antiviral activity can be identified by comparing the CPE in drug treated cultures to that observed in untreated infected cells.

Assay Protocol

1. Cells

NCTC clone 1469, a derivative of mouse liver, ATCC No. CCL 9.1.

2. Virus

Mouse hepatitis virus strain MHV-A59 classified as a coronavirus, ATCC No. 764.

3. Media

Growth Media
NCTC 135
10% horse serum
2% L-glutamine (200 mM)
1% nonessential amino acids (NEAA) (100X)
1% sodium pyruvate (110 mg/liter) (100X)
50 μg gentamicin Maintenance medium Dulbecco's modified Eagle's minimum essential medium in Earle's balanced salt solution (4500 mg/liter glucose) (D-EMEM)
5% fetal bovine serum
2% L-glutamine (200 mM)
1% nonessential amino acids (NEAA) (100X)
1% sodium pyruvate (110 mg/liter) (100X)
50 ug/ml gentamicin Trypsin solution 0.5 mg/ml trypsin, 0.2 mg/ml EDTA.4 Na, and 1.1 mg/ml glucose in
Dulbecco's phosphate buffered saline without CaCl$_2$ and MgCl.6 H$_2$O
(PBS)

Methylene blue stain
5 grams methylene blue/liter
50% ethanol:water

4. Growth of NCTC 1469 cell line

Confluent cultures are exposed briefly to the trypsin solution and flasks are shaken hard to remove cells from the plastic. For a 150 cm$^2$ flask, add 4 ml of trypsin solution and reduce volume for smaller cell areas. Subcultures for cell maintenance are seeded at $10 \times 10^6$ cells in 40 ml growth medium for 150 cm$^2$ tissue culture flask. Cells are subcultured twice a week.

5. Antiviral assay

Twenty four- well plates (16 mm diameter/well) are seeded between $7.5 \times 10^5$ and $1 \times 10^6$ cells in 1 ml growth medium per well. Plates are incubated 24 hours at 37° C. in 5% CO$_2$. The growth medium is removed and the cultures are infected with 0.2 ml A59 diluted in PBS with calcium and magnesium to contain approximately 100 infectious doses of virus. Plates are incubated at 37° C. for 1 hour in 5% CO$_2$. Viral supernatants are removed and replaced with maintenance medium only or medium containing drug solutions. The drug solutions are prepared by adding diluted samples to glass tubes and allowing solvents to evaporate. Ten lambda of dimethyl sulfoxide is added to each tube to solubilize drug material and 1 ml maintenance medium is added to the tube. The fluid from each tube is transferred to the NCTC 1469 cells infected with A59 virus.

Cytopathic effects can be observed in 12 hours. Plates are routinely read at 24 hours after fixation and staining with methylene blue dye. Drug cytotoxicity Cell viability is used to determine drug cytotoxicity.
100% = complete cell destruction
75% = partial cell destruction
50% = partial cell destruction
25% = partial cell destruction
0% = no cytotoxicity Antiviral activity
+++ = absence of CPE and cell fusion
++ = partial inhibition
+ = partial inhibition
± = marginal inhibition
0 = no protection The fifty per cent minimum inhibitory concentration (MIC$_{50}$) is determined by estimating the per cent reduction in CPE compared to the controls from the inhibition values with +++ = 100% reduction, ++ = 75%, + = 50%, ± = 25%, and − = no reduction in plaque number compared to control.

TABLE 1

| Cpd. | Con | HSV-1 | | VSV | |
|---|---|---|---|---|---|
| | | CV-1 | AVA | CV-1 | AVA |
| 1 + 2 | 40 | 12 | +++ | 12 | + |
| | 20 | 12 | +++ | 12 | + |
| 3 | 40 | 16 | | 16 | |
| | 20 | 14 | ++ | 12 | ++ |
| 4 + 5 | 40 | 16 | | 16 | |
| | 20 | 16 | | 16 | |
| 6 + 7 | 40 | 16 | | 16 | |
| | 20 | 14 | + | 12 | + |
| 8 | 40 | 8 | — | 8 | — |
| | 20 | 8 | | 8 | — |

TABLE 2

| | | HSV-1 | | A-59 | |
|---|---|---|---|---|---|
| 1 | 200 | 14 | +++ | 0 | +++ |
| 2 | 200 | 10 | +++ | 0 | +++ |
| 8 | 200 | 14 | — | 100 | |

In the tables, Con. is the concentration of the test compound in μg/well; CV-1 is the zone of inhibition in mm; and AVA is antiviral activity measured as noted above.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

In accordance with the invention, pharmaceutical compositions comprise, as active ingredient, an effective amount of one or more of the new compounds and one or more non-toxic, pharmaceutically acceptable carriers or diluents. Examples of such carriers for use in the invention include ethanol, dimethyl sulfoxide, glycerol, silica, alumina, starch equivalent carriers and diluents. While effective amounts may vary, as conditions in which such compositions are used vary, a minimal dosage required for antiviral activity is generally between 50 and 200 micrograms against 25–80 plaque-forming units of virus. To provide for the administration of such dosages for the desired therapeutic treatment, new pharmaceutical compositions of the invention will advantageously comprise between about 0.1% and 45%, and especially, 1 and 25%, by weight of the total of one or more of the new compounds based on the weight of the total composition including carrier or diluent.

The embodiments of the invention in which an exclusive property or privilege is claimed are defined as follows:

1. A compound of the formulae:

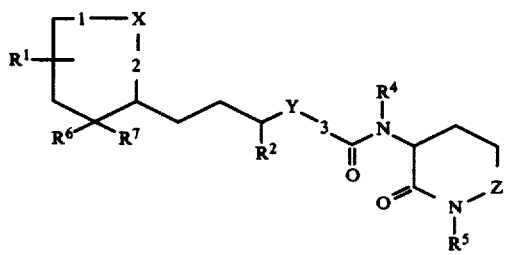
I

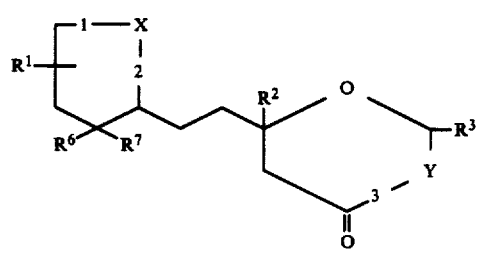
II

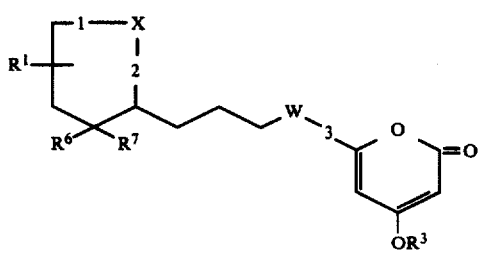
III wherein $X = -1-CH_2-\underset{\underset{CH_2}{\|}}{C}-2-$ or $-1-CH=\underset{\underset{CH_3}{|}}{C}-2-$ $Y = -CH_2-3-$ or $=CH-3-$ $Z = -CH_2-$ or $-CH_2-CH_2-$ $W = -\underset{\underset{R^1}{|}}{CH}-3-$ or $=\underset{\underset{R^1}{|}}{C}-3-$ and $R^1, R^2, R^3, R^4, R^5, R^6, R^7 = H$ or lower alkyl.

2. A compound of the formula:

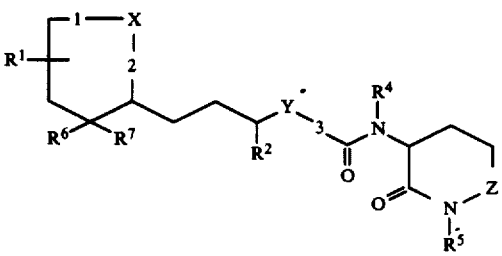

wherein $X = -1-CH_2-\underset{\underset{CH_2}{\|}}{C}-2-$ or $-1-CH=\underset{\underset{CH3}{|}}{C}-2-$ $Y = -CH_2-3-$ or $=CH-3-$ $Z = CH_2-$ or $-CH_2-CH_2-$ and $R^1, R^2, R^3, R^4, R^5, R^6, R^7 = H$ or lower alkyl.

3. A compound of claim 1 of the formula:

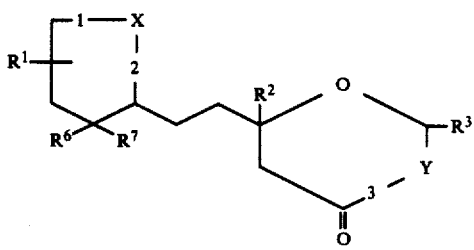

wherein $X = -1-CH_2-\underset{\underset{CH_2}{\|}}{C}-2-$ or $-1-CH=\underset{\underset{CH3}{|}}{C}-2-$ $Y = -CH_2-3-$ or $=CH-3-$ and $R^1, R^2, R^3, R^4, R^5, R^6, R^7 = H$ or lower alkyl.

4. A compound of claim 1 of the formula:

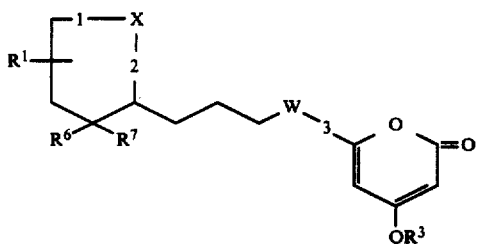

wherein

X = —1—CH₂—C—2— or —1—CH=C—2—
              |                    |
              CH3

W = —CH—3— or =C—3—
       |            |
       R¹           R¹ and

R¹, R², R³, R⁴, R⁵, R⁶, R⁷=H or lower alkyl.

5. A pharmaceutical composition comprising between about 0.1% to 45% by weight, based on the total weight of said composition, as an active ingredient one or more of the compounds of claim 1 and a non-toxic pharmaceutically acceptable carrier of diluent.

6. A pharmaceutical composition comprising between about 0.1% to 45% by weight, based on the total weight of said composition, as an active ingredient oneor more of the compounds of claim 2 and a non-toxic pharmaceutically acceptable carrier of diluent.

7. A pharmaceutical composition comprising between about 0.1% to 45% by weight, based on the total weight of said composition, as an active ingredient one or more of the compounds of claim 3 and a non-toxic pharmaceutically acceptable carrier of diluent.

8. A pharmaceutical composition comprising between about 0.1% to 45% by weight, based on the total weight of said composition, as an active ingredient one or more of the compounds of claim 4 and a non-toxic pharmaceutically acceptable carrier of diluent.

9. A compound of the formula:

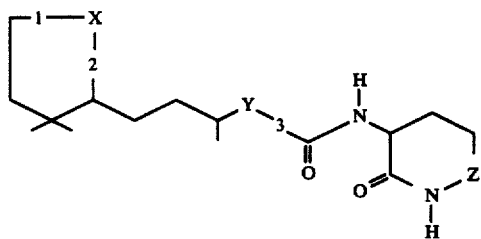

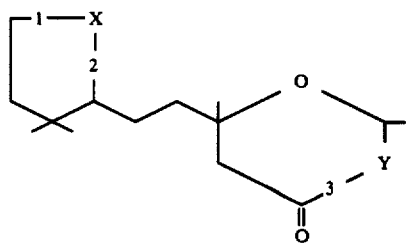

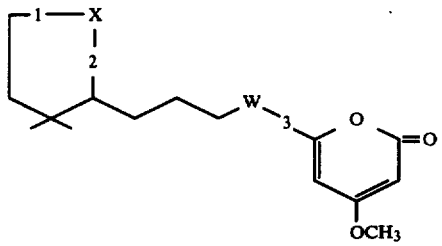

wherein

X = —1—CH₂—C—2— or —1—CH₂=C—2—
              ||                       |
              CH₂                      CH₃

Y= —CH₂—3— or =CH—3—

Z= —CH₂— or —CH₂—CH₂—

W= —CH—3— or =C=3—

10. A substantially pure compound of claim 9 of the formula:

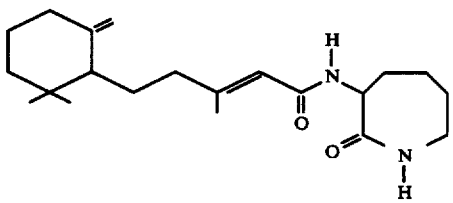

11. A substantially pure compound of claim 9 of the formula:

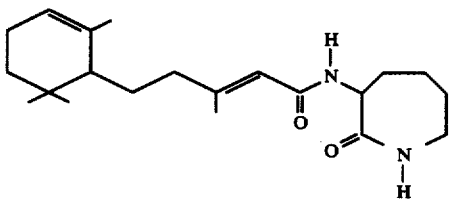

12. A substantially pure compound of claim 9 of the formula:

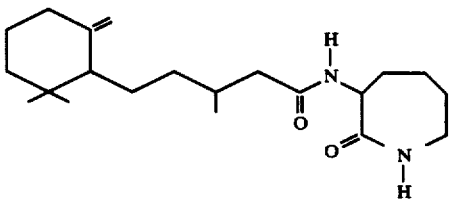

13. A substantially pure compound of claim 9 of the formula:

14. A substantially pure compound of claim 9 of the formula:

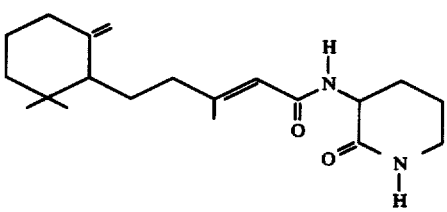

15. A substantially pure compound of claim 9 of the formula:

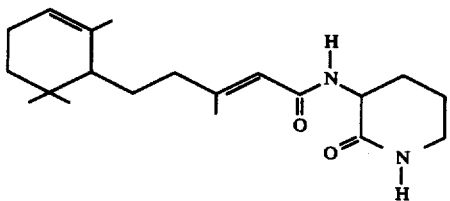

16. A substantially pure compound of claim 9 of the formula:

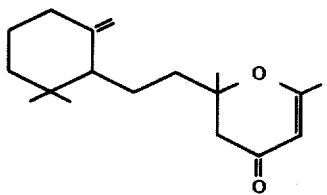

17. A substantially pure compound of claim 9 of the formula:

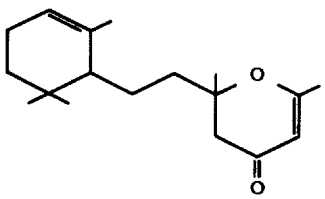

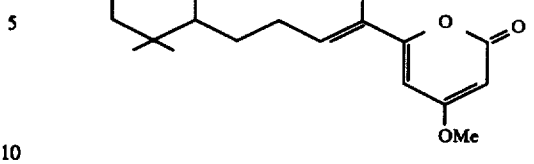

18. A pharmaceutical composition comprising between about 0.1% and 45% by weight, based on the total weight of said composition, as an active ingredient one or more of the compounds of claim 9 and a non-toxic pharmaceutically acceptable carrier or diluent.

19. A pharmaceutical composition comprising between about 0.1% and 45% by weight, based on the total weight of said composition, as an active ingredient the compound of claim 18 and a non-toxic pharmaceutically acceptable carrier or diluent.

20. A pharmaceutical composition comprising between about 0.1% and 45% by weight, based on the total weight of said composition, as an active ingredient the compound of claim 11 and a non-toxic pharmaceutically acceptable carrier or diluent.

21. A pharmaceutical composition comprising between about 0.1% and 45% by weight, based on the total weight of said composition, as an active ingredient the compound of claim 12 and a non-toxic pharmaceutically acceptable carrier or diluent.

22. A pharmaceutical composition comprising between about 0.1% and 45% by weight, based on the total weight of said composition, as an active ingredient the compound of claim 13 and a non-toxic pharmaceutically acceptable carrier or diluent.

23. A pharmaceutical composition comprising between about 0.1% and 45% by weight, based on the total weight of said composition, as an active ingredient the compound of claim 14 and a non-toxic pharmaceutically acceptable carrier or diluent.

24. A pharmaceutical composition comprising between about 0.1% and 45% by weight, based on the total weight of said composition, as an active ingredient the compound of claim 15 and a non-toxic pharmaceutically acceptable carrier or diluent.

25. A pharmaceutical composition comprising between about 0.1% and 45% by weight, based on the total weight of said composition, as an active ingredient the compound of claim 16 and a non-toxic pharmaceutically acceptable carrier or diluent.

26. A pharmaceutical composition comprising between about 0.1% and 45% by weight, based on the total weight of said composition, as an active ingredient the compound of claim 17 and a non-toxic pharmaceutically acceptable carrier or diluent.

* * * * *

UNITED STATES PATENT AND TRADEMARK OFFICE
CERTIFICATE OF CORRECTION

PATENT NO. : 4,908,445
DATED : March 13, 1990
INVENTOR(S) : Kenneth L. Rinehart, Ashok D. Patil It is certified that error appears in the above–identified patent and that said Letters Patent is hereby corrected as shown below:

| | | |
|---|---|---|
| olumn 3: | line 60: | "extract I)" should read --extract II)--. |
| | line 64: | "[60" should read --[$\alpha$ --. |
| olumn 4: | line 35: | "1" should read --3--. |
| | lines 45 to 52: | Delete. |
| olumn 7: | line 6: | "$^1$NMR" should read --$^1$H NMR--. |
| | line 60: | "of 1 dissolved" should read --of 1 was dissolved--. |
| olumn 9: | line 30: | "cell fushion" should read --cell fusion--. |
| | line 50: | "50 $\mu$g" should read --50 $\mu$g/ml--. |
| olumn 12: | line 37: | "$CH_2$-" should read ---$CH_2$---. |
| olumn 13: | line 15: | omitted, should read --$CH_2$--. |
| olumn 14: | line 22: | "=C=" should read --=C---. |

Signed and Sealed this

Ninth Day of July, 1991

*Attest:*

HARRY F. MANBECK, JR.

*Attesting Officer*   Commissioner of Patents and Trademarks